(12) United States Patent
Breyne et al.

(10) Patent No.: US 6,399,791 B1
(45) Date of Patent: Jun. 4, 2002

(54) NAPHTHOPYRAN DERIVATIVES, COMPOSITIONS AND (CO) POLYMER MATRICES CONTAINING SAME

(75) Inventors: Olivier Breyne, Borneil-sur-marne; You-Ping Chan, Lyons, both of (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/341,967

(22) PCT Filed: Mar. 17, 1998

(86) PCT No.: PCT/US98/05235

§ 371 (c)(1),
(2), (4) Date: Jul. 20, 1999

(87) PCT Pub. No.: WO98/42663

PCT Pub. Date: Oct. 1, 1998

Related U.S. Application Data

(60) Provisional application No. 60/054,987, filed on Aug. 6, 1997.

(30) Foreign Application Priority Data

Mar. 21, 1997 (FR) ............................... 97 03459

(51) Int. Cl.⁷ .................. C07D 311/92; A61K 31/352; G02F 1/03; G02F 1/07
(52) U.S. Cl. .................. 549/389; 514/454; 359/241
(58) Field of Search .................. 549/389; 514/454; 359/241

(56) References Cited

U.S. PATENT DOCUMENTS

| | | |
|---|---|---|
| 3,627,690 A | 12/1971 | Casella et al. |
| 4,826,977 A | 5/1989 | Heller et al. |
| 4,931,221 A | 6/1990 | Heller |
| 5,200,116 A | 4/1993 | Heller |
| 5,458,814 A | 10/1995 | Kumar et al. |
| 5,573,712 A | 11/1996 | Kumar et al. |
| 5,656,206 A | 8/1997 | Knowles et al. |

FOREIGN PATENT DOCUMENTS

| | | | |
|---|---|---|---|
| EP | 0 246 114 A | 11/1987 | |
| EP | 0 401 958 A | 12/1990 | |
| EP | 0 835 870 A1 | 4/1998 | |
| WO | 92/01959 A | 2/1992 | |
| WO | WO 95/16215 | 6/1995 | |
| WO | WO 96/04576 | 2/1996 | |
| WO | 97 21698 | 6/1997 | ......... C07D/311/78 |
| WO | WO 98/14443 | 4/1998 | |

OTHER PUBLICATIONS

JP 04,112,885 to Tanaka et al., abstract No. 117:201990f, in Chemical Abstracts, 117(74):717 (1992) (Abstract Only).
Edwards et al., Hypoxyxylerone. A Novel Green Pigment from the Fungus *Hypoxylon fragiforme* (Pers.: Fries) Kickx, *J. Chem. Soc. Chem. Commun.*, 1009–1010 (1991).

*Primary Examiner*—T. A. Solola
(74) *Attorney, Agent, or Firm*—Angela N. Nwaneri; Peter Rogalskyj

(57) ABSTRACT

For subject, the present invention has novel naphthopyran derivatives of formula:

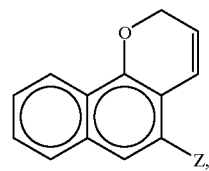

optionally substituted in position(s) 2, 3, 4, 6, 7, 8, 9 or/and 10; the substituent Z in position 5 being of formula —C(R1)(R2)(OR3).

The invention also relates to compositions and (co)polymer matrices containing such derivatives. Said derivatives have interesting photochromic properties.

24 Claims, No Drawings

NAPHTHOPYRAN DERIVATIVES, COMPOSITIONS AND (CO) POLYMER MATRICES CONTAINING SAME

The present application is 371 of PCT/US98/05235, filed Mar. 17, 1998, which claims the benefit of U.S. Provisional Patent Application Serial No. 60/054,987, filed Aug. 6, 1997, and of French Patent Application No. 97 03459, filed Mar. 21, 1997.

The present invention relates to novel compounds, naphthopyran derivatives, which possess, in particular, photochromic properties. It relates also to photochromic compositions and photochromic ophthalmic articles (for example lenses) containing said novel compounds.

The photochromic compounds are able to change color under the influence of a poly- or monochromatic light (for example UV) and to regain their initial color when the light irradiation ceases, or under the influence of temperature and/or of poly- or monochromatic light different from the first.

The photochromic compounds find applications in various fields, for example for the manufacture of ophthalmic lenses, contact lenses, solar protection lenses, filters, camera optical systems or photographic apparatus optical systems or optical systems of other optical devices, and observation optical systems, glazings, decorative objects, bill elements or even for the storage of information by optical inscription (coding).

In the field of ophthalmic optics, and in particular in the spectacles trade, a photochromic lens, comprising one or more photochromic compounds, must possess:

a high transmission in the absence of ultraviolets, a low transmission (high colorability) under solar irradiation, adapted coloration and discoloration kinetics, a tint acceptable to the consumer (gray or brown, preferably) with, preferably, a maintenance of the chosen tint during coloration and discoloration of the lens, a maintenance of the performances, i. e. the properties in a temperature range of 0–40° C., an important durability, since these desired objectives are sophisticated corrective lenses and are therefore expensive.

These lens characteristics are, in fact, determined by the active photochromic compounds that it contains; these compounds must in addition be perfectly compatible with the organic or inorganic support making up the lens.

It is in other respects to be noted that obtaining a gray or brown tint may necessitate the use of at least two photochromes of different colors, i.e. having distinct maximal absorption wavelengths in the visible. This association further imposes other requirements of the photochromic compounds. In particular, the coloration and discoloration kinetics of the (two or more) associated active photochromic compounds must be roughly identical. The same applies for their stability with time and, also, the same applies for their compatibility with a plastic or inorganic support.

Among the numerous photochromic compounds described in the prior art, benzopyrans or naphthopyrans described in the patents U.S. Pat. No. 3,567,605, U.S. Pat. No. 3,627,690, U.S. Pat. No. 4,818,096, U.S. Pat. No. 4,826,977, U.S. Pat. No. 5,200,116, U.S. Pat. No. 5,238,981, U.S. Pat. No. 5,458,814 and in the Research Disclosure No. 36144, may be cited, which are of the following formula:

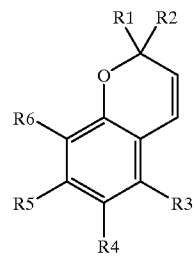

These compounds claim to satisfy the specifications defined above. In reality, if these compounds really have one or more of the basic properties sought after, such as a high transmission in the absence of ultraviolets and a high colorability under solar irradiation, all the compounds described hitherto have not the complete combination of properties sought after which are necessary for the production of satisfactory articles which can be manufactured industrially.

It is to the credit of the Applicant to have found, in a surprising way, that the presence of a group of the type —C(R1)(R2)(OR3) in position 5 of 2H-naphtho[1,2-b] pyrans enabled lowering their discoloration kinetics. This type of molecules, novel per se, adapts well in association with yellow and/or orange and/or red complementary photochromes in order to give gray or brown tints.

The present invention thus has, for first subject, naphthopyran derivatives of formula:

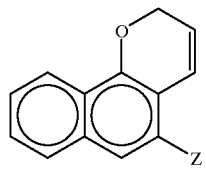

optionally substituted in position(s) 2, 3, 4, 6, 7, 8, 9 or/and 10; the substituent Z in position 5 being of formula —C(R1)(R2)(OR3) in which:

R1 and R2, identical or different represent independently:
  hydrogen or a linear alkyl group having 1 to 6 carbon atoms;

R3 represents:
  hydrogen,
  an R11 group, R11 representing:
    a linear or branched alkyl group having 1 to 12 carbon atoms;
    a cycloalkyl or bicycloalkyl group having 3 to 12 carbon atoms;
    an aralkyl group, the alkyl group, linear or branched, having 1 to 3 carbon atoms and the aryl group being selected from a phenyl group or a naphthyl group optionally substituted with at least one linear or branched alkyl group having 1 to 6 carbon atoms or a linear or branched alkoxy group having 1 to 6 carbon atoms;
    a $CH_2CO(R12)$ group, R12 being an OH, a linear or branched alkyl group having 1 to 6 carbon atoms, a linear or branched alkoxy group having 1 to 6 carbon atoms, or a phenoxy group;
    a $CH_2CN$ group;
  a CO(R13) group, R13 representing:
    a linear or branched alkyl group, having 1 to 12 carbon atoms;

a cycloalkyl or bicycloalkyl group having 3 to 12 carbon atoms;
a vinyl or 2-propenyl group (having therefore $OR_3$=$OCOR_{13}$ which represents respectively an acryloyl or methacryloyl group);
a phenyl or naphthyl group optionally substituted with at least one linear or branched alkoxy group having 1 to 6 carbon atoms;
a phenoxy group;
a secondary amine group NH(R14), R14 representing a linear or branched alkyl group having 1 to 12 carbon atoms, a cycloalkyl group having 3 to 12 carbon atoms, a phenyl group optionally substituted with at least one linear or branched alkyl group having 1 to 6 carbon atoms.

Said naphthopyran derivatives include the naphthopyran substituted in position 5 with Z, as well as all the other compounds of corresponding formulae, which have at least one substituent on the —CH and —CH$_2$ groups of the formula below. Among said derivatives, those which are disubstituted on the carbon a to oxygen of the pyran ring are preferred. Said a carbon may therefore be an asymmetric carbon. The compounds of the invention may therefore be in the form of racemic mixtures (generally) or they may be pure isomers of such derivatives having an asymmetric carbon.

In the context of its first subject, such as defined above, the present application relates to naphthopyran derivatives of formula (I) below:

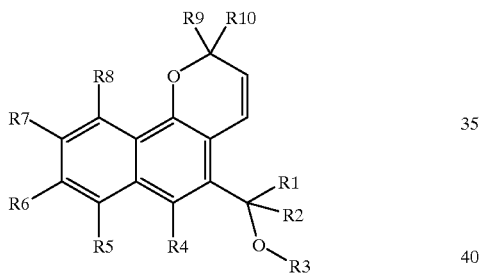

wherein:
R1, R2 and R3 are such as defined above;
R4 to R8, identical or different, represent independently:
hydrogen;
a halogen, notably fluorine, chlorine or bromine;
a linear or branched alkyl group having 1 to 12 carbon atoms;
a linear or branched alkoxy group having 1 to 12 carbon atoms;
a linear or branched alkenyl group having from 1 to 12 carbon atoms, notably a vinyl or allyl group;
an aryl or heteroaryl group having 6 to 24 carbon atoms or 4 to 24 carbon atoms respectively in its basic structure and at least one heteroatom selected from sulfur, oxygen and nitrogen; said basic structure being optionally substituted with at least one substituent selected from:
a halogen, notably fluorine, chlorine and bromine;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms, notably a fluoroalkyl group of this type;

an —NH$_2$ group;
an —NHR group, R representing a linear or branched alkyl group having 1 to 6 carbon atoms;
a

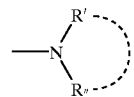

group, R' and R", which are identical or different, representing independently a linear or branched alkyl group having 1 to 6 carbon atoms or, together with the nitrogen atom to which they are attached, form a 5 to 7 membered ring which may have at least one other heteroatom selected from oxygen, sulfur and nitrogen, said nitrogen being optionally substituted with an R'" group which is a linear or branched alkyl group having 1 to 6 carbon atoms;
an amine or amide group: —NH$_2$, —NHR, —CONH$_2$, —CONHR,

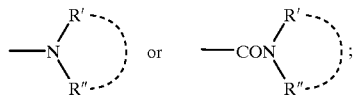

R, R', R" being respectively of their definitions given above for the amine substituents of the values R4 to R8: aryl or heteroaryl;
a —OCO(R15) or —COO(R15) group, R15 representing a linear or branched alkyl group having 1 to 6 carbon atoms, a cycloalkyl group having 3 to 6 carbon atoms, or a phenyl group optionally substituted with at least one of the substituents listed above for the values of R4 to R8: aryl or heteroaryl;
a methacryloyl or a acryloyl group;
an epoxy group of formula:

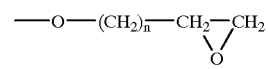

wherein n=1, 2 or 3;
R9 and R10, which are identical or different, represent independently:
hydrogen,
a linear or branched alkyl group having 1 to 12 carbon atoms;
a cycloalkyl or bicycloalkyl group having 3 to 12 carbon atoms;
an aryl or heteroaryl group having 6 to 24 carbon atoms or 4 to 24 carbon atoms respectively in its basic structure and at least one heteroatom selected from sulfur, oxygen and nitrogen; said basic structure being optionally substituted with at least one substituent selected from:
a halogen, notably fluorine, chlorine and bromine;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms, notably a fluoroalkyl group of this type;
an —NH$_2$ group;

an —NHR group, R representing a linear or branched alkyl group having 1 to 6 carbon atoms;

a

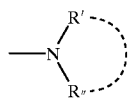

group, R' and R", which are identical or different, representing independently a linear or branched alkyl group having 1 to 6 carbon atoms or, together with the nitrogen atom to which they are attached, form a 5 to 7 membered ring which may have at least one other heteroatom selected from oxygen, sulfur and nitrogen, said nitrogen being optionally substituted with an R''' group which is a linear or branched alkyl group having 1 to 6 carbon atoms;

an aralkyl or heteroaralkyl group, the alkyl group, which is linear or branched, having from 1 to 4 carbon atoms and the aryl and heteroaryl groups having the definitions given above for R9, R10: aryl or heteroaryl groups; or said two substituents R9 and R10 together form an adamantyl, norbornyl, fluorenylidene, di($C_1$–$C_6$) alkylanthracenylidene or a spiro($C_5$–$C_6$) cycloalkylanthracenylidene group; said group being optionally substituted with at least one of the substituents listed above for R4 to R8 or R9, R10: aryl or heteroaryl group.

Among the naphthopyran derivatives of the invention, those that are preferred (for their photochromic properties) are of formula (I) above wherein $R_5$ and $R_7$ are alkoxy ($C_1$–$C_{12}$ alkoxy) groups, advantageously methoxy groups.

Among said naphthopyran derivatives of the invention, those of formula (I) above are also preferred wherein $R_9$ and $R_{10}$ represent independently a substituent selected from those aryl or heteroaryl groups whose basic structure is selected from those of the phenyl, naphthyl, biphenyl, pyridyl, furyl, benzofuryl, dibenzofuryl, N—($C_1$–$C_6$)alkyl carbazole, thienyl, benzothienyl, dibenzothienyl groups.

Among the substituents of the naphthopyran derivatives of the invention, there are some which have and/or form at least one polymerizable and/or cross-linkable reactive group. The presence of such reactive groups may reveal to be opportune. Thus, the present invention includes, in its first object, the class of the 2H-naphtho[1,2-b]pyran derivatives substituted in position 5 with the specific —C(R1)(R2)(OR3) group and whose structure includes at least one polymerization and/or cross-linking reactive group; it being possible for said group to notably consist of an alkenyl group, which is advantageously of the vinyl or allyl type, a methacryloyl, acryloyl or epoxy group.

Thus, the compounds of the invention which belong to said class may be apprehended as monomers, of a different nature or not, which are able to react with themselves or with other comonomers in order to form homopolymers and/or copolymers, which bear a photochromic functionality (insofar as said monomers of the invention bear said photochromic functionality) and which possess mechanical properties of macromolecules.

It follows that another subject of the present invention is formed by these homopolymers or copolymers, linear or branched, which are at least in part constituted by naphthopyran derivatives of the invention.

Along the same lines, the above-mentioned naphthopyran derivatives can be envisaged to be cross-linking agents having reactive functions which are able to allow bridging between polymer chains of photochromic nature or not. The reticulates, which are able to be so obtained, also constitute another subject of the present invention.

The preparation of the naphthopyran derivatives according to the invention do not present any particular difficulties. Said naphthopyran derivatives can be obtained, in a general manner, by condensation of a 1-naphthol, having a hydrogen in position 2, an ester group in position 3, and which are optionally substituted in the other positions of the naphthalenic ring, and either propargylic alcohol or a substituted derivative of said alcohol (the condensation reaction may, according to said variant, be carried out in solvents such as toluene or tetrahydrofuran in the presence of a catalyst such as paratoluenesulfonic acid, chloroacetic acid or acidic alumina), or acrolein or a derivative of said acrolein (in the presence of titanium tetraethoxide).

These synthetic routes are conventional and have been described in the references of the prior art cited above as well as in EP-A-0 562 915.

With reference more particularly to the compounds of the invention of formula (I), the synthetic routes are schematized below.

Step 1: Synthesis of the 1-naphthol derivative

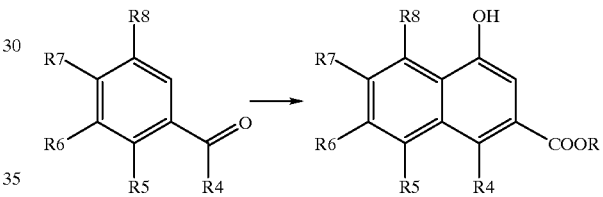

(see for example: Aust. J. Chem. 1987, 40, 1737 and Org. React. 1951, 6, 1).

Step 2: Synthesis of the pyran ring

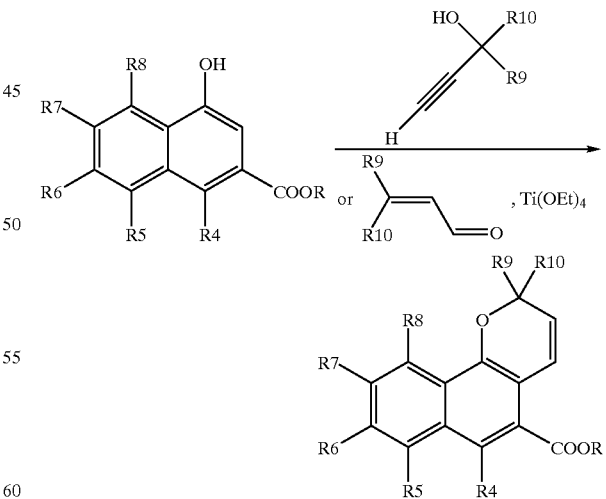

This step 2 may also be carried out with the reagents indicated and a naphthol whose ester function is converted beforehand into an alcohol.

Step 3: according to the final compound desired, the syntheses may be carried out in the following manner:

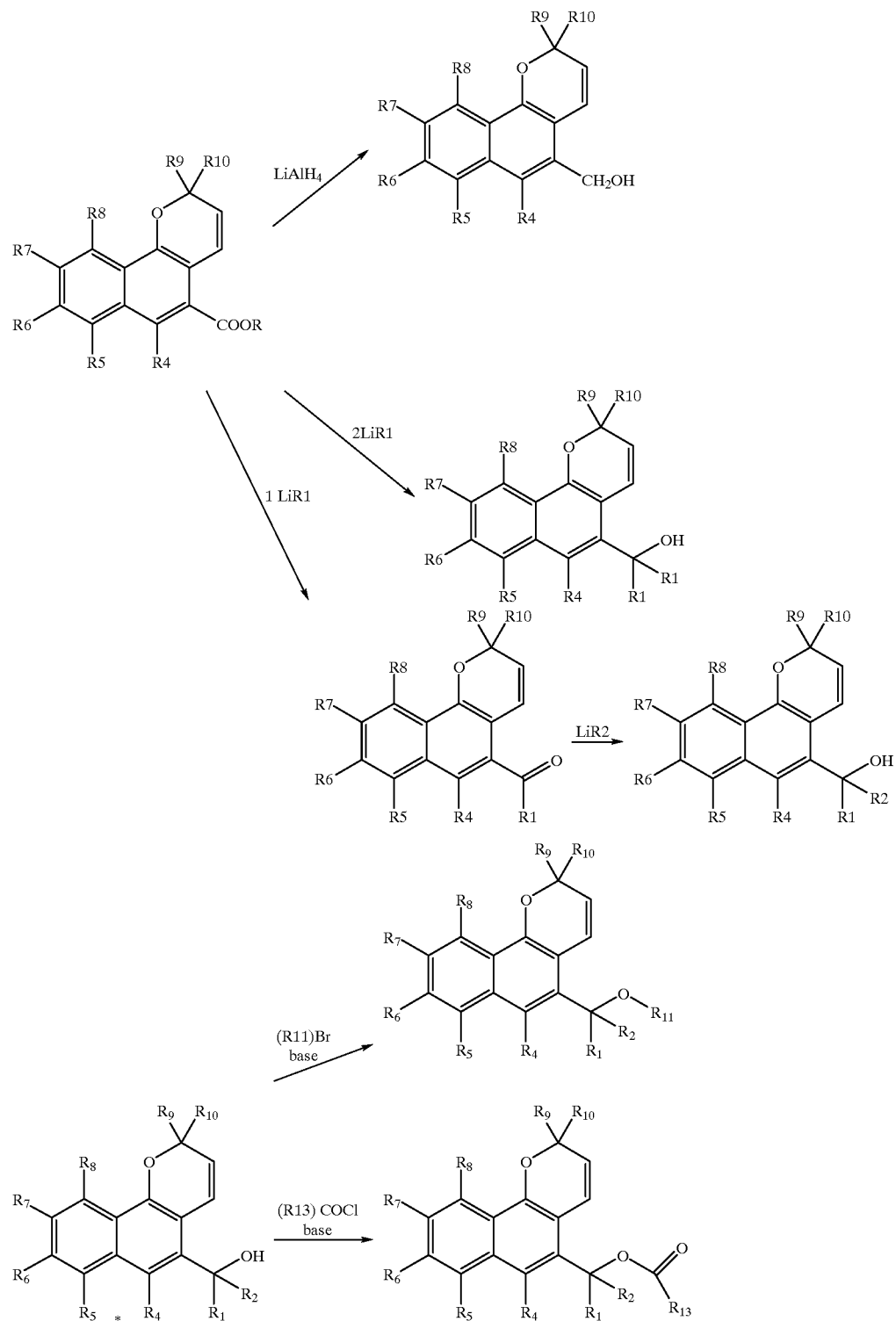

-continued

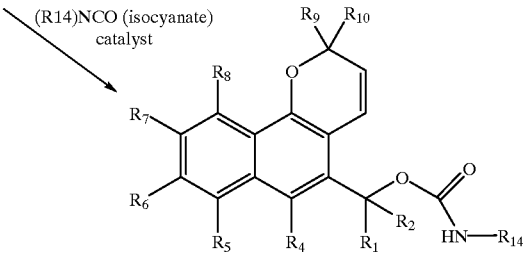

*In this formula, $R_1$ and $R_2$, identical or different represent independently H or a ($C_1$–$C_6$) alkyl group.

It is to be noted that the conversions in Step 3 above are conventional and well-known to the person skilled in the art.

It is to the credit of the Applicant to have prepared and tested the original naphthopyran derivatives described above; said derivatives possessing particularly advantageous photochromic properties. More specifically, these novel compounds are endowed with a high colorability, with faster discoloration kinetics than their homologues with a hydrogen or a methyl group in position 5 (instead of and in the place of the Z substituent).

These compounds are, in other respects, compatible with support matrices of organic polymer or of inorganic material, both in the form included in the matrix and in the form of a coating.

In solution or in a polymer matrix, the compounds according to the invention are colorless or slightly colored in the initial state and rapidly develop an intense coloration under a UV light (365 nm) or a light source of the solar type. Finally, they regain their initial color once the irradiation ceases.

According to another of its subjects, the present invention relates to the use of said compounds of the invention as photochromic agents. In other terms, the Applicant hereby proposes:

novel photochromic compounds, which consist of the naphthopyran derivatives such as defined above, taken separately or in a mixture with themselves and/or with at least one other photochromic compound of another type and/or with at least one non-photochromic colorant;

novel photochromic compositions, which comprise at least one naphthopyran derivative such as defined above and/or at least one (co)polymer and/or reticulate including in its structure at least one of said naphthopyran derivatives of the invention. Such photochromic compositions can include at least one other photochromic compound of another type and/or at least one non-photochromic colorant and/or at least one stabilizer.

Said photochromic compounds of another type, non-photochromic colorants, stabilizers are prior art products known to the person skilled in the art.

In the context of the present invention, the associations of photochromic compounds of the invention, and/or associations of photochromic compounds of the invention and photochromic compounds of another type according to prior art, are convenient for generating gray or brown tints.

The compounds of the invention, notably as pbotochromic compounds, can be used in solution. Thus, a photochromic solution can be obtained by solubilizing the compound in an organic solvent such as toluene, dichloromethane, tetrahydrofuran or ethanol. The solutions obtained are generally colorless and transparent. Once exposed to solar light, they develop a high coloration and regain the colorless state once they are placed in a zone of less exposure to solar rays or, in other terms, when they are no longer submitted to UV. It is sufficient, in general, for a very low concentration of product (in the order of 0.01 to 5% by weight) to obtain an intense coloration.

The compounds of the invention can also be used as a photochromic material uniformnly dispersed in the mass or in the surface of a polymer matrix. In fact, the most interesting applications of the compounds of the invention are those in which the photochrome is dispersed uniformly within or on the surface of a polymer, a copolymer or a mixture of polymers. The (co)polymer matrix which comprises said photochrome of the invention (at least one, in the free form, in the form of a (co)polymer and/or reticulate, and/or in the form of a photochromic composition, such as defined above) constitutes another subject of the present invention.

The implementation processes which can be envisaged for obtaining such a matrix are very varied. Among those known to the person skilled in the art, it can. be cited, for example, the diffusion in the (co)polymer, from a suspension or solution of the photochrome, in a silicone oil, in an aliphatic or aromatic hydrocarbon, in a glycol, or from another polymer matrix. The diffusion is commonly carried out at a temperature of 50 to 200° C. for a period of time of 15 minutes to some hours, according to the nature of the polymer matrix. Another implementation technique consists in mixing the photochrome in a formulation of polymerizable materials, depositing this mixture on a surface or in a mold and then carrying out the copolymerization. These implementation techniques and others are described in the article by Crano et al. "Spiroxazines and their use in photochromic lenses" published in Applied Photochromic Polymer Systems, Ed. Blackie and Son Ltd—1992.

In accordance with a variant of this subject of the invention, it is also possible to envisage grafting the photochromes on the (co)polymers. Thus, the invention also relates to the (co)polymers grafted with at least one of the photochromes described hereinbefore. The expression "(co)polymer matrix comprising at least one photochrome of the invention" means therefore both matrices which comprise said photochrome in their masses and in their surfaces, and matrices grafted with said photochrome.

As examples of polymer materials preferred for optical applications of the photochromic compounds according to the invention, the following products can be mentioned:

alkyl, cycloalkyl, aryl or arylalkyl mono-, di-, tri- or tetra-acrylate or mono-, di-, tri- or tetra-methacrylate optionally halogenated or comprising at least one ether and/or ester and/or carbonate and/or carbamate and/or thiocarbamate and/or urea and/or amide group, polystyrene, polyether, polyester, polycarbonate (e.g. polycarbonate of bisphenol-A, polycarbonate of diallyl diethylene glycol), polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate or polyvinylbutyral, copolymers of two or more types of monomer or mixtures of polymers referred to above, preferably polycarbonate-polyurethane, poly(meth)acrylate-polyurethane, polystyrene-poly(meth)acrylate or even polystyrene-polyacrylonitrile, advantageously a mixture of polyester and polycarbonate or poly(meth)acrylate.

The amount of photochrome used in the (co)polymer matrix depends on the degree of darkening desired. In a customary manner, an amount of it is used which is between 0.001 and 20% by weight. The photochromic compounds according to the invention can be used alone or in a mixture with other products in order to form a composition which can be presented in solid or liquid form, for example in solution or in dispersion, as has already been indicated above. These compositions, which constitute a subject of the invention as already indicated above, can therefore comprise the compounds of the invention and other complementary photochromic compounds which allow obtaining dark colorations, for example gray or brown, desired by the public in applications such as the solar or ophthalmic spectacles trade. These complementary photochromic compounds can be those known to the person skilled in the art and described in the literature, for example chromenes (U.S. Pat. No. 3,567,605, U.S. Pat. No. 5,238,981, WO-A-94 22 850, EP-A-562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colorants which allow adjusting the tint, and/or one or more stabilizers, like for example an antioxidant, and/or one or more anti-UV agents, and/or one or more anti-radical agents, and/or one or more chemical excited states deactivators.

These additives can notably allow the improvement of the durability of said compositions.

According to another of its aspects relative to the application of the compounds of the invention (naphthopyran derivatives), the present invention has also ophthalmic articles for subject, such as solar or ophthalmic spectacles trade articles, comprising at least one compound according to the invention and/or at least one (co)polymer and/or reticulate formed, at least in part, from compounds of the invention and/or at least one composition comprising at least one compound of the invention, such as defined above, and/or at least one matrix, such as defined above, of an organic polymer material or inorganic material or even of an organic-inorganic hybrid material incorporating therein at least one compound of the invention.

In practice, the articles which are most particularly aimed at by the present invention are the photochromic solar or ophthalmic lenses, glazings (panes for buildings, for locomotive engines, automobiles), optical devices, decorative articles, solar protection articles, information storages.

The present invention is illustrated by the following examples of synthesis and of photochromic validation, of compounds of the invention (2H-naphtho[1,2-b]pyran derivatives substituted in position 5 with a specific group).

EXAMPLES

SYNTHESIS AND PROPERTIES OF PHOTOCHROMIC COMPOUNDS 1 TO 4 OF THE INVENTION

Example 1

Synthesis of Compound (1)

Step 1: 5,7-dimethoxy-3-methoxycarbonyl-1-acetoxynaphthalene is synthesized according to the procedure described in Org. React. 1951, 6, 1; by the reaction of 2,4-dimethoxybenzaldehyde and dimethyl succinate in the presence of potassium tert-butoxide followed by a cyclization in acetic anhydride in the presence of sodium acetate. 5,7-dimethoxy-3-methoxycarbonyl-1-naphthol is then obtained after deacetylation of the preceding product in HCl(2N)/methanol under reflux for 3 hours.

Step 2: The naphthol derivative from the preceding step (4.2 g) is reacted with 1-(p-dimethylaminophenyl)-1-phenyl-2-propyn-1-ol (4.0 g) in 80 ml of xylene under reflux overnight. The method described in EP-A-250 193 is followed for the synthesis of the propynol derivative. The intermediate photochromic compound of the invention obtained is then purified by chromatography on an alumina column eluted with a THF/diisopropyl ether mixture. The yield is 27%. The structure is confirmed by $^1$H NMR.

Step 3: Reduction of the ester function in position 5 of the product from the preceding step (300 mg) is carried out by lithium aluminum hydride (LiAlH$_4$; 33 mg) in 5 ml of anhydrous THF for 20 minutes at 0° C. Compound (1) of Table 1 below is obtained in a yield of 76% after hydrolysis and purification. Its structure is confirmed by $^1$H NMR spectroscopy.

Example 2

Compound (2) of said Table 1 below is obtained from compound (1) by reaction with acetyl chloride in the presence of triethylamine. Compound (2) is obtained in a yield of 81% after purification. Its structure is confirmed by $^1$H NMR spectroscopy.

Example 3

Compound (3) of said Table 1 below is obtained in a manner analogous to that used for compound (2) by using benzoyl chloride instead of acetyl chloride in the last step. The yield is 24% after purification. The structure of said compound (3) is confirmed by $^1$H NMR spectroscopy.

Example 4

200 mg of the compound obtained in step 2 of Example 1 are reacted with 9 molar equivalents of MeLi (in solution in cumene/THF:9/1) in 10 ml of THF for 2 hours at room temperature. The medium is hydrolyzed by a solution of ammonium chloride and compound (4) of Table 1 below is extracted with toluene. After purification by crystallization in diisopropyl ether, the desired compound is obtained in a yield of 40%. Its structure is confirmed by $^1$H NMR spectroscopy.

Example 5

Analysis of the photochromic properties in solution in THF. Each photochromic compound of the invention (5 mg) (compounds (1) to (4) of the Table 1 below) is dissolved in 50 ml of THF and part of the solution is placed in a quartz cell of 1 cm of optical path. The solution is irradiated with a UV source of 365 nm and the UV-visible spectrum is recorded. The discoloration kinetics are themselves measured by the decrease of the absorption at the λmax of the activated form after irradiation (T½=time for the absorbance to decrease by half).

A prior art compound C1 (described in FR-A-96 09384) is treated in the same way. Said compound was obtained by a synthetic route analogous to that illustrated in the Examples above: by coupling 1-(p-dimethylaminophenyl)-1-phenyl-2-propyn-1-ol with 5,7-dimethoxy-3-methyl-1-naphthol; said 1-naphthol being prepared according to the method described in J. Org. Chem. 1986, vol. 51, p 271–273 (Sibi et al).

TABLE 1

Photochromic properties in solution in THF

| compound | structure | λmax | T1/2 |
|---|---|---|---|
| 1 | 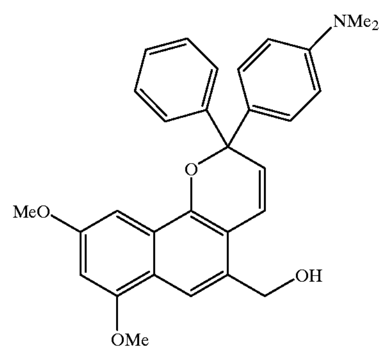 | 565 nm | 41 s |
| 2 | 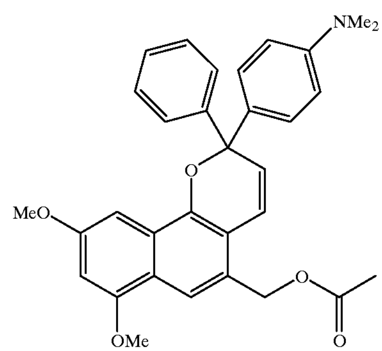 | 564 | 28 s |
| 3 | 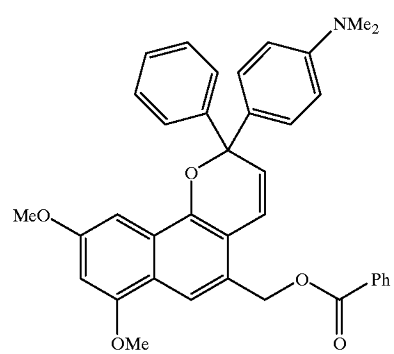 | 570 nm | 15 s |

TABLE 1-continued

Photochromic properties in solution in THF

| compound | structure | λmax | T1/2 |
|---|---|---|---|
| 4 | (structure shown) | 548 | 9 s |
| C1 (FR 96 09384) | (structure shown) | 561 nm | 70 s |

Example 6

Incorporation of the Compounds in a Polyacrylate 5 mg of compounds (1) and (3) of the invention and C1 of the prior art are solubilized in 10 g of tetraethoxyl bisphenol A dimethacrylate (marketed under the name of Diacryl 121 by the Akzo Company) containing also 40 mg of 2,2'-azobis(2-methylbutyronitrile). The solution is then degassed, regassed with argon, and poured into a glass lens mold of 8 cm in diameter and 2 mm thickness. The mold is then placed in an oven at 70° C. for 12 hours. After turning out, a rigid and transparent lens is obtained. Under irradiation of the solar type, the glass rapidly develops an intense violet coloration and becomes colorless again in the shade The photochromic characteristics are given in Table 2 below.

TABLE 2

Photochromic properties in acrylate matrix

| properties | compound (1) | compound (3) | compound (C1) |
|---|---|---|---|
| Visible λmax | 496 and 580 nm | 492 and 586 nm | 492 and 582 nm |
| Initial transmission* | 86% | 80% | 81% |
| Transmission after 15 minutes irradiation* | 13% | 18% | 6% |
| Transmission after 5 minutes of discoloration in the dark* | 28% | 36% | 16% |

*transmissions measured at 560 nm

It is demonstrated by these examples that the compounds of the invention have discoloration kinetics which are faster than their prior art analogues. Moreover, it has been shown by us that it is relatively easy to control the discoloration kinetics by the choice of the specific group in position 5 of the naphthopyran skeleton. These molecules adapt well in association with the blue and/or violet and/or red complementary photochromes of equivalent discoloration kinetics for obtaining gray or brown tints.

What is claimed is:

1. A naphthopyran having formula (I) below:

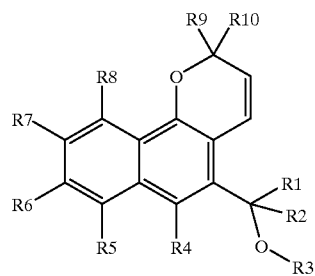

wherein
R1 and R2, which are identical or different, represent independently a linear alkyl group having 1 to 4 carbon atoms;
a R3 represents:
 hydrogen or
 an R11 group, R11 represent:
  a linear or branched alkyl group having 1 to 12 carbon atoms;
  a cycloalkyl or bicycloalkyl group having 3 to 12 carbon atoms;

an aralkyl group, the alkyl group, of which is linear or branched and has 1 to 3 carbon atoms and the aryl group of which is selected from a phenyl group or a naphthyl group optionally substituted with at least one linear or branched alkyl group having 1 to 6 carbon atoms or a linear or branched alkoxy group having 1 to 6 carbon atoms;

a CH$_2$CO(R12) group, R12 being an OH, a linear or branched alkyl group having 1 to 6 carbon atoms, a linear or branched alkoxy group having 1 to 6 carbon atoms, or a phenoxy group; or a CH$_2$CN group; or a CO(R13) group, R13 represent:
a linear or branched alkyl group having 1 to 12 carbon atoms;
a cycloalkyl or bicycloalkyl group having 3 to 12 carbon atoms;
a vinyl or 2-propenyl group;
a phenyl or naphthyl group optionally substituted with at least one linear or branched alkoxy group having 1 to 6 carbon atoms; or
a phenoxy group; or
a secondary amine group NH(R14), R14 representing a linear or branched alkyl group having 1 to 12 carbon atoms, a cycloalkyl group having 3 to 12 carbon atoms, or a phenyl group optionally substituted with at least one linear or branched alkyl group having 1 to 6 carbon atoms;

R4 to R8, identical or different, represent independently:
hydrogen;
a halogen;
a linear or branched alkyl group having 1 to 12 carbon atoms;
a linear or branched alkoxy group having 1 to 12 carbon atoms;
a linear or branched alkenyl group having from 1 to 12 carbon atoms;
an aryl or heteroaryl group, said heteroaryl group further having at least one heteroatom selected from sulfur, oxygen and nitrogen; said aryl or heteroaryl group being optionally substituted with at least one substituent selected from:
a halogen;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms;
an —NH$_2$ group;
an —NHR group, R representing a linear or branched alkyl group having 1 to 6 carbon atoms; or
a

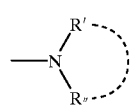

group, R' and R", which are identical or different, represent independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms;

an amine or amide group: —NH$_2$, —NHR, —CONH$_2$, —CONHR,

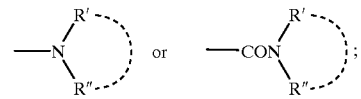

in which R represents a linear or branched alkyl group having 1 to 6 carbon atoms and in which R' and R", which are identical or different, independently represent a linear or branched alkyl group having 1 to 6 carbon atoms or, together with the nitrogen atom to which they are attached, form a 5 to 7 membered ring which optionally contains at least one other heteroatom selected from oxygen, sulfur, and nitrogen, said nitrogen being optionally substituted with an R'" group which is a linear or branched alkyl group having 1 to 6 carbon atoms;

a —OCO(R15) or —COO(R15) group, R15 representing a linear or branched alkyl group having 1 to 6 carbon atoms, a cycloalkyl group having 3 to 6 carbon atoms, or a phenyl group optionally substituted with at least one substituent selected from the group consisting of:
a halogen;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms;
an —NH$_2$ group;
an —NHR group, R representing a linear or branched alkyl group having 1 to 6 carbon atoms; and
a

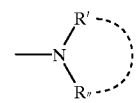

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms;

a methacryloyl or a acryloyl group; or an epoxy group of formula:

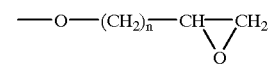

wherein n=1, 2 or 3; and

R9 and R10, which are identical or different, represent independently:
hydrogen, a linear or branched alkyl group having 1 to 12 carbon atoms;
a cycloalkyl or bicycloalkyl group having 3 to 12 carbon atoms;
an aryl or heteroaryl group, said heteroaryl group further having at least one heteroatom selected from sulfur, oxygen and nitrogen; said aryl or heteroaryl group being optionally substituted with at least one substituent selected from:
a halogen;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms;
an —NH$_2$ group;
an —NHR group, R representing a linear or branched alkyl group having 1 to 6 carbon atoms; or
a

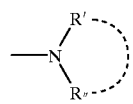

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R''' group which is a linear or branched alkyl group having 1 to 6 carbon atoms; or
an aralkyl or heteroaralkyl group, the alkyl group, which is linear or branched, having from 1 to 4 carbon atoms and the aryl and heteroaryl groups being optionally substituted with a substituent selected from the group consisting of:
a halogen;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms;
an —NH$_2$ group;
an —NHR group, R representing a linear or branched alkyl group having 1 to 6 carbon atoms; and
a

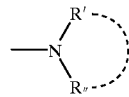

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R''' group which is a linear or branched alkyl group having 1 to 6 carbon atoms; or
said two substituents R9 and R10 together form an adamantyl group, a norbornyl group, a fluorenylidene group, a di(C$_1$–C$_6$)alkylanthracenylidene group, or a spiro anthracenylidene group bearing a (C$_5$–C$_6$)cycloalkyl moiety; said group being optionally substituted with at least one substituent selected from the group consisting of:
a halogen;
a linear or branched alkyl group having 1 to 6 carbon atoms;
a linear or branched alkoxy group having 1 to 6 carbon atoms;
a linear or branched haloalkyl or haloalkoxy group having 1 to 6 carbon atoms;
an —NH$_2$ group;
an —NHR group, R representing a linear or branched alkyl group having 1 to 6 carbon atoms; and
a

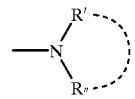

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R''' group which is a linear or branched alkyl group having 1 to 6 carbon atoms.

2. A naphthopyran according to claim 1, wherein each of R5 and R7 are alkoxy groups.

3. A naphtholyran according to claim 1, wherein R9 and R10 are independently an aryl or heteroaryl group whose basic structure is selected from those of the phenyl, naphthyl, biphenyl, pyridyl, furyl, benzofuryl, dibenzofuryl, N-(C$_1$–C$_6$)alkyl carbazole, thienyl, benzothienyl, or dibenzothienyl groups.

4. A naphthopyran according to claim 3, wherein at least one of R5 and R7 is a methoxy group.

5. A naphthopyran according to claim 2, wherein each of R5 and R7 is a methoxy group.

6. A naphthopyran according to claim 2, wherein R9 and R10 are independently an aryl or heteroaryl group selected from phenyl, naphthyl, biphenyl, pyridyl, furyl, benzofuryl, dibenzofuryl, N-(C$_1$–C$_6$)alkyl carbazole, thienyl, benzothienyl, and dibenzothienyl groups.

7. A naphthopyran according to claim 1, wherein R5 is a linear or branched alkoxy group having 1 to 12 carbon atoms.

8. A naphthopyran according to claim 7, wherein R7 is a linear or branched alkoxy group having 1 to 12 carbon atoms.

9. A naphthopyran according to claim 8, wherein each of R4, R6, and R8 is a hydrogen.

10. A naphthopyran according to claim 1, wherein R5 is an alkoxy group.

11. A naphthopyran according to claim 1, wherein R5 is a methoxy group.

12. A naphthopyran according to claim 11, wherein each of R4, R6, and R8 is a hydrogen.

13. A naphthopyran according to claim 1, wherein each of R4, R6, and R8 is a hydrogen.

14. A naphthopyran according to claim 1, wherein each of R1 and R2 is a methyl group.

15. A naphthopyran according to claim 14, wherein R5 is an alkoxy group.

16. A naphthopyran according to claim 14, wherein R5 is a linear or branched alkoxy group having 1 to 12 carbon atoms.

17. A naphthopyran according to claim 14, wherein R5 is a methoxy group.

18. A naphthopyran according to claim 14, wherein each of R5 and R7 is an alkoxy group.

19. A naphthopyran according to claim 14, wherein each of R5 and R7 is a linear or branched alkoxy group having 1 to 12 carbon atoms.

20. A naphthopyran according to claim 14, wherein each of R5 and R7 is a methoxy group.

21. A naphthopyran having formula (I) below:

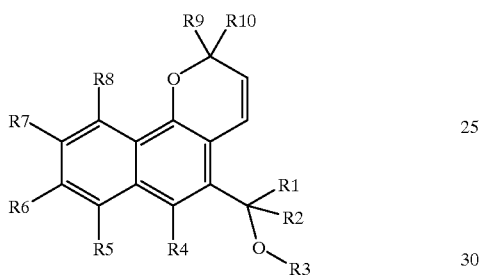

wherein
R1 and R2 each represent a methyl group;
R3 represents:
  hydrogen or
  an R11 group, R11 represent:
    a linear or branched alkyl group having 1 to 12 carbon atoms;
    a cycloalkyl or bicycloalkyl group having 3 to 12 carbon atoms;
    an aralkyl group, the alkyl group, of which is linear or branched and has 1 to 3 carbon atoms and the aryl group of which is selected from a phenyl group or a naphthyl group optionally substituted with at least one linear or branched alkyl group having 1 to 6 carbon atoms or a linear or branched alkoxy group having 1 to 6 carbon atoms;
    a CH$_2$CO(R12) group, R12 being an OH, a linear or branched alkyl group having 1 to 6 carbon atoms, a linear or branched alkoxy group having 1 to 6 carbon atoms, or a phenoxy group; or
    a CH$_2$CN group; or
  a CO(R13) group, R13 representing:
    a linear or branched alkyl group having 1 to 12 carbon atoms;
    a cycloalkyl or bicycloalkyl group having 3 to 12 carbon atoms;
    a vinyl or 2-propenyl group;
    a phenyl or naphthyl group optionally substituted with at least one linear or branched alkoxy group having 1 to 6 carbon atoms; or
    a phenoxy group; or
  a secondary amine group NH(R14), R14 representing a linear or branched alkyl group having 1 to 12 carbon atoms, a cycloalkyl group having 3 to 12 carbon atoms, or a phenyl group optionally substituted with at least one linear or branched alkyl group having 1 to 6 carbon atoms;
R4 to R8, identical or different, represent independently:
  hydrogen;
  a halogen;
  a linear or branched alkyl group having 1 to 12 carbon atoms;
  a linear or branched alkoxy group having 1 to 12 carbon atoms;
  a linear or branched alkenyl group having from 1 to 12 carbon atoms;
  an aryl or heteroaryl group, said heteroaryl group further having at least one heteroatom selected from sulfur, oxygen and nitrogen; said aryl or heteroaryl group being optionally substituted with at least one substituent selected from:
    a halogen;
    a linear or branched alkyl group having 1 to 6 carbon atoms;
    a linear or branched alkoxy group having 1 to 6 carbon atoms;
    a linear or branched haloalkyl or haloalkoxy group having 1 to 6 carbon atoms;
    an —NH$_2$ group;
    an —NHR group, R representing a linear or branched alkyl group having 1 to 6 carbon atoms; or
    a

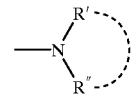

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms;
an amine or amide group: —NH$_2$, —NHR, —CONH$_2$, —CONHR,

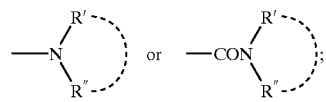

in which R represents a linear or branched alkyl group having 1 to 6 carbon atoms and in which R' and R", which are identical or different, independently represent a linear or branched alkyl group having 1 to 6 carbon atoms or, together with the nitrogen atom to which they are attached, form a 5 to 7 membered ring which optionally contains at least one other heteroatom selected from oxygen, sulfur, and nitrogen, said nitrogen being optionally substituted with an R'" group which is a linear or branched alkyl group having 1 to 6 carbon atoms;
a —OCO(R15) or —COO(R15) group, R15 representing a linear or branched alkyl group having 1 to 6 carbon atoms, a cycloalkyl group having 3 to 6 carbon atoms, or a phenyl group optionally substituted with at least one substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

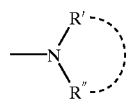

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms;

a methacryloyl or a acryloyl group; or an epoxy group of formula:

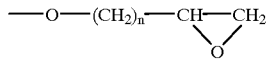

wherein n 1, 2 or 3; and

R9 and R10, which are identical or different, represent independently:

hydrogen, a linear or branched alkyl group having 1 to 12 carbon atoms;

a cycloalkyl or bicycloalkyl group having 3 to 12 carbon atoms;

an aryl or heteroaryl group, said heteroaryl group further having at least one heteroatom selected from sulfur, oxygen and nitrogen; said aryl or heteroaryl group being optionally substituted with at least one substituent selected from:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; or a

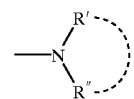

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms; or an aralkyl or heteroaralkyl group, the alkyl group, which is linear or branched, having from 1 to 4 carbon atoms and the aryl and heteroaryl groups being optionally substituted with a substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

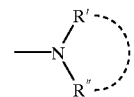

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms; or said two substituents R9 and R10 together form an adamantyl group, a norbornyl group, a fluorenylidene group, a di(C$_1$–C$_6$)alkylanthracenylidene group, or a spiro anthracenylidene group bearing a (C$_5$–C$_6$)cycloalkyl moiety; said group being optionally substituted with at least one substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

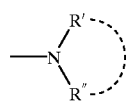

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R''' group which is a linear or branched alkyl group having 1 to 6 carbon atoms.

22. A naphthopyran having formula (I) below:

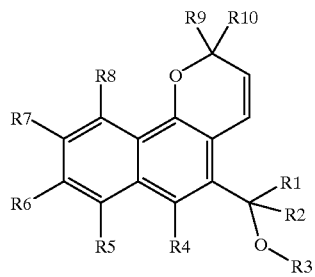

wherein
R1 and R2 each represent a methyl group;
R3 represents:
  hydrogen or
  an R11 group, R11 representing:
    a linear or branched alkyl group having 1 to 12 carbon atoms;
    a cycloalkyl or bicycloalkyl group having 3 to 12 carbon atoms;
    an aralkyl group, the alkyl group, of which is linear or branched and has 1 to 3 carbon atoms and the aryl group of which is selected from a phenyl group or a naphthyl group optionally substituted with at least one linear or branched alkyl group having 1 to 6 carbon atoms or a linear or branched alkoxy group having 1 to 6 carbon atoms;
    a $CH_2CO(R12)$ group, R12 being an OH, a linear or branched alkyl group having 1 to 6 carbon atoms, a linear or branched alkoxy group having 1 to 6 carbon atoms, or a phenoxy group; or
    a $CH_2CN$ group; or
  a CO(R13) group, R13 representing:
    a linear or branched alkyl group having 1 to 12 carbon atoms;
    a cycloalkyl or bicycloalkyl group having 3 to 12 carbon atoms;
    a vinyl or 2-propenyl group;
    a phenyl or naphthyl group optionally substituted with at least one linear or branched alkoxy group having 1 to 6 carbon atoms; or
    a phenoxy group; or
  a secondary amine group NH(R14), R14 representing a linear or branched alkyl group having 1 to 12 carbon atoms, a cycloalkyl group having 3 to 12 carbon atoms, or a phenyl group optionally substituted with at least one linear or branched alkyl group having 1 to 6 carbon atoms;

R5 represents a linear or branched alkoxy group having 1 to 12 carbon atoms;
R4 and R6 to R8, identical or different, represent independently:
  hydrogen;
  a halogen;
  a linear or branched alkyl group having 1 to 12 carbon atoms;
  a linear or branched alkoxy group having 1 to 12 carbon atoms;
  a linear or branched alkenyl group having from 1 to 12 carbon atoms;
  an aryl or heteroaryl group, said heteroaryl group further having at least one heteroatom selected from sulfur, oxygen and nitrogen; said aryl or heteroaryl group being optionally substituted with at least one substituent selected from:
    a halogen;
    a linear or branched alkyl group having 1 to 6 carbon atoms;
    a linear or branched alkoxy group having 1 to 6 carbon atoms;
    a linear or branched haloalkyl or haloalkoxy group having 1 to 6 carbon atoms;
    an $—NH_2$ group;
    an —NHR group, R representing a linear or branched alkyl group having 1 to 6 carbon atoms; or
  a

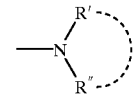

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R''' group which is a linear or branched alkyl group having 1 to 6 carbon atoms;
an amine or amide group: $—NH_2$, —NHR, $—CONH_2$, —CONHR,

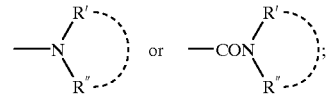

in which R represents a linear or branched alkyl group having 1 to 6 carbon atoms and in which R' and R", which are identical or different, independently represent a linear or branched alkyl group having 1 to 6 carbon atoms or, together with the nitrogen atom to which they are attached, form a 5 to 7 membered ring which optionally contains at least one other heteroatom selected from oxygen, sulfur, and nitrogen, said nitrogen being optionally substituted with an R''' group which is a linear or branched alkyl group having 1 to 6 carbon atoms;
a —OCO(R15) or —COO(R15) group, R15 representing a linear or branched alkyl group having 1 to 6 carbon atoms, a cycloalkyl group having 3 to 6 carbon atoms, or a phenyl group optionally substituted with at least one substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

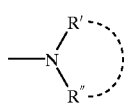

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms;

a methacryloyl or a acryloyl group; or an epoxy group of formula:

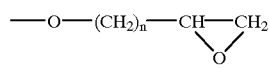

wherein n=1, 2 or 3; and

R9 and R10, which are identical or different, represent independently:

hydrogen, a linear or branched alkyl group having 1 to 12 carbon atoms;

a cycloalkyl or bicycloalkyl group having 3 to 12 carbon atoms;

an aryl or heteroaryl group, said heteroaryl group further having at least one heteroatom selected from sulfur, oxygen and nitrogen; said aryl or heteroaryl group being optionally substituted with at least one substituent selected from:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; or a

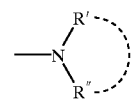

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms; or an aralkyl or heteroaralkyl group, the alkyl group, which is linear or branched, having from 1 to 4 carbon atoms and the aryl and heteroaryl groups being optionally substituted with a substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

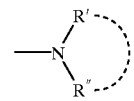

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms; or said two substituents R9 and R10 together form an adamantyl group, a norbornyl group, a fluorenylidene group, a di(C$_1$–C$_6$)alkylanthracenylidene group, or a spiro anthracenylidene group bearing a (C$_5$–C$_6$)cycloalkyl moiety; said group being optionally substituted with at least one substituent selected from the group consisting of:

a halogen;

a linear or branched alkyl group having 1 to 6 carbon atoms;

a linear or branched alkoxy group having 1 to 6 carbon atoms;

a linear or branched haloalkyl or haloalkoxy group having 1 to 6 carbon atoms;

an —NH$_2$ group;

an —NHR group, R representing a linear or branched alkyl group having 1 to 6 carbon atoms; and a

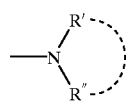

group, R' and R", which are identical or different, representing independently a linear or branched alkyl group having 1 to 6 carbon atoms or, together with the nitrogen atom to which they are attached, forming a 5 to 7 membered ring which optionally contains at least one other heteroatom selected from oxygen, sulfur and nitrogen, said nitrogen being optionally substituted with an R'" group which is a linear or branched alkyl group having 1 to 6 carbon atoms.

23. A composition characterized in that said composition comprises at least two naphthopyrans according to claim 2, or characterized in that said composition comprises at least one naphthopyran according to claim 2 and at least one other photochromic compound of another type, or characterized in that said composition comprises at least one naphthopyran according to claim 1 and at least one non-photochromic colorant.

24. Photochromic composition, characterized in that it comprises;
   at least one naphthopyran according to claim 1, and
   at least one other photochromic compound of another type and/or at least one non-photochromic colorant and/or at least one stabilizer.

* * * * *